(12) United States Patent
Wang et al.

(10) Patent No.: US 7,417,036 B2
(45) Date of Patent: Aug. 26, 2008

(54) CRYSTAL FORM OF ADEFOVIR DIPIVOXIL AND ITS PREPARATION

(75) Inventors: Guocheng Wang, Tianjin (CN); Xinbo Lu, Tianjin (CN); Qinxuan Liu, Tianjin (CN); Yu Tang, Tianjin (CN); Liping Yang, Tianjin (CN)

(73) Assignee: Tianjin Kinsly Pharmaceutical Co. Ltd. (CN)

( * ) Notice: Subject to any disclaimer, the term of this patent is extended or adjusted under 35 U.S.C. 154(b) by 358 days.

(21) Appl. No.: 10/534,602

(22) PCT Filed: Nov. 11, 2003

(86) PCT No.: PCT/CN03/00949

§ 371 (c)(1),
(2), (4) Date: Jun. 13, 2005

(87) PCT Pub. No.: WO2004/043972

PCT Pub. Date: May 27, 2004

(65) Prior Publication Data

US 2006/0025384 A1 Feb. 2, 2006

(30) Foreign Application Priority Data

Nov. 12, 2002 (CN) ............................. 02 1 48923

(51) Int. Cl.
*C07F 9/6561* (2006.01)
*A61K 31/675* (2006.01)

(52) U.S. Cl. ...................................... 514/81; 544/244
(58) Field of Classification Search ........................ None
See application file for complete search history.

(56) References Cited

U.S. PATENT DOCUMENTS

| 4,142,059 | A | | 2/1979 | Greene et al. ................ 562/606 |
| 5,663,159 | A | * | 9/1997 | Starrett et al. ................ 514/181 |

FOREIGN PATENT DOCUMENTS

| EP | 1 083 164 A1 | 3/2001 |
| GB | 2 008 588 A | 6/1979 |
| WO | WO 99/04774 | 2/1999 |
| WO | WO 00/35460 | 6/2000 |

OTHER PUBLICATIONS

Abstract for CN 1435420 (Aug. 13, 2003).*
Abstract for CN 1425673 (Jun. 25, 2003).*
Abstract for CN 1396170 (Feb. 2, 2003).*
Abstract for CN1374314 (Oct. 16, 2002).*
Abstract for CN1421449 (Jun. 4, 2003).*
Abstract for CN1421451 (Jun. 4, 2003).*
Barditch-Crovo P. et al., Journal of Infectious Diseases, 176 (2): 406, 1997.
Starrett et al., Journal of Med. Chem., 37: 1857-1864, 1994.

* cited by examiner

*Primary Examiner*—Mark L Berch
(74) *Attorney, Agent, or Firm*—Ballard Spahr Andrews & Ingersoll, LLP (57) ABSTRACT

A new crystal form of adefovir dipivoxil {9-[2-[bis(pivaloyloxy)-methoxy]-phosphinyl]-methoxyl]-ethyl]-adenime} and its composition is disclosed, as is a method to prepare the crystal comprising placing adefovir dipivoxil in a round bottom flask, adding organic solvent and dissolivng adefovir dipivoxil ultrasonically to form and adefovir dipivoxil solution, and spray drying the adefovir dipivoxil solution.

7 Claims, 4 Drawing Sheets

CRYSTAL FORM OF ADEFOVIR DIPIVOXIL AND ITS PREPARATION

CROSS REFERENCE TO RELATED APPLICATIONS

The present application claims priority to China Patent Application No 02148923.8, filed Nov. 12, 2002, which application is incorporated herein fully by this reference.

TECHNICAL FIELD

The present invention relates to a new crystalline form of a compound and its composition, and in particular, to a new crystalline form of adefovir dipivoxil with the nomenclature of 9-[2-[bis(pivaloyloxy)-methoxy]phosphinyl]methoxy)ethyl]adenine and a composition containing that new crystalline form. The present invention also discloses a process for preparing this new crystalline form.

BACKGROUND OF THE INVENTION

The new antiviral drug, adefovir dipivoxil (hereinafter "AD"), is a nucleotide reverse transcriptase inhibitor with the nomenclature of 9-[2-[bis(pivaloyloxy)-methoxy]phosphinyl]methoxy)ethyl]adenine, which exhibits a marked invivo antiviral activity against both HIV and HBV. For more information about its antiviral activities, see Barditch-Crovo P et al, J Infect Dis, 176(2): 406, 1997, and Starrett et al, J Med Chem, 37:1857-1864, 1994.

Studies show that the AD in nature exists in two forms: amorphous and crystal. PCT patent application "pharmaceutical formulations" (International Publication NO. W00035460A) discloses a more stable AD pharmaceutical formulations comprising anhydrous crystalline AD and dihydrate crystalline AD and an alkaline excipient. Another application, W09904774A, discloses compositions containing one or more crystalline AD, wherein the AD comprises the following crystalline forms with different melting points: the anhydrous crystalline form, the hydrated form, the solvate form, and the salt crystalline form.

It is well known that different crystalline forms of a drug compound have different melting points, solubility, and density of said drug compound. At the same time, the fluidity and flexibility of crystals of said compound and the dissolution rate, stability, and effectiveness of said crystals in a pharmaceutical formulation may differ from one to another. For example, although the γ-type of indolacin is less stable, it has better performance in solubility, bioavailability and pharmacology than that of the α and β type. In addition, different crystalline forms may be enantiotropic under certain conditions. For instance, during the process of wet granulation, the drug may be dissolved in a solvent added and recrystallized in the later drying step to obtain a new crystalline form, which may affect the dissolution of the drug and the uniformity of the pharmaceutical formulation containing this drug. Therefore it is necessary to select a crystalline form with a suitable stability during manufacture and storage. Taking insulin zinc as an example, the dissolution rate of its stable form is slower than that of its metastable one. Thus a suspension of short, medium or long term release may be obtained by adjusting the proportion of these two crystalline forms. Therefore, it is not always necessary to adopt the most stable crystalline form in pharmaceutical industry, which depends on a lot of factors, such as the clinical uses, producing costs and cycles, as well as techniques and so on.

CONTENTS OF THE INVENTION

When carrying out studies on the AD, the inventor of this invention surprisingly discovered a novel crystalline form of AD exhibiting good dissolution, distribution, and flowability. In addition, it may facilitate manufacturing and formulating of the composition containing the AD.

In a first aspect this invention relates to a novel crystal of AD or a novel crystalline form of AD, which is characterized in that the X-ray powder diffraction pattern of the said novel crystalline form shows a peak(s) expressed in terms of $2\theta$ at about 3.60, and/or about 7.28, and/or about 15.08, and/or about 17.24, and/or about 17.96, and/or about 20.12, and/or about 22.24.

In another aspect this invention relates to a pharmaceutical composition comprising crystalline AD and pharmaceutically acceptable carriers, which is characterized in that the X-ray powder diffraction pattern of said crystalline AD shows a peak(s) expressed in terms of $2\theta$ at about 3.60, and/or about 7.28, and/or about 15.08, and/or about 17.24, and/or about 17.96, and/or about 20.12, and/or about 22.24.

In another aspect this invention provides a process for producing the new AD crystal, which comprises dissolving the AD made by the known methods or commercially available AD in an organic solvent, and then spray drying the resultant organic solution to obtain the new AD crystal.

In a further aspect this invention provides a composition comprising at least 70 wt % of this novel crystal AD or novel crystalline form of AD.

Figure 1:
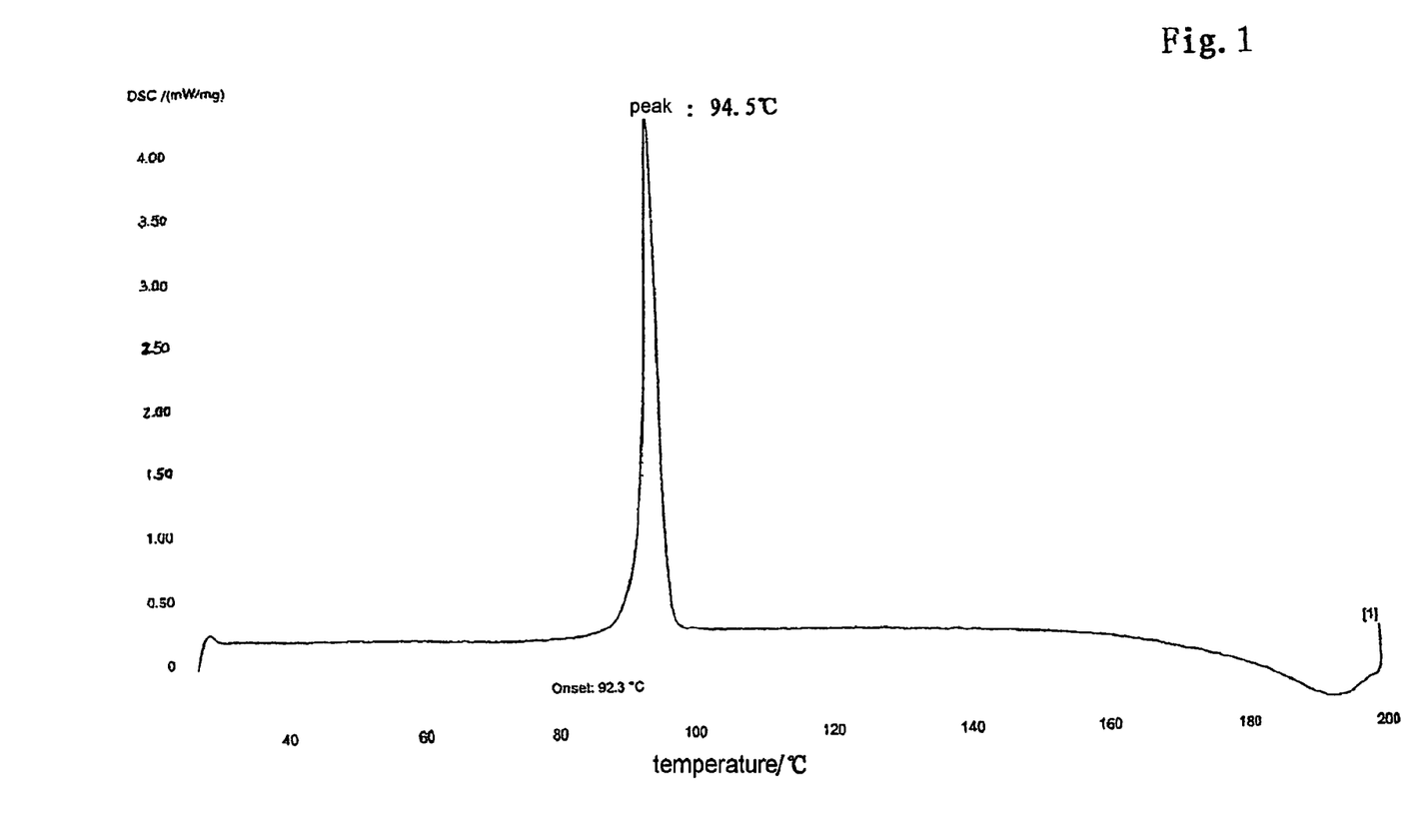
FIG. 1 shows DSC thermogram of the crystalline AD of the present invention.
Figure 2:
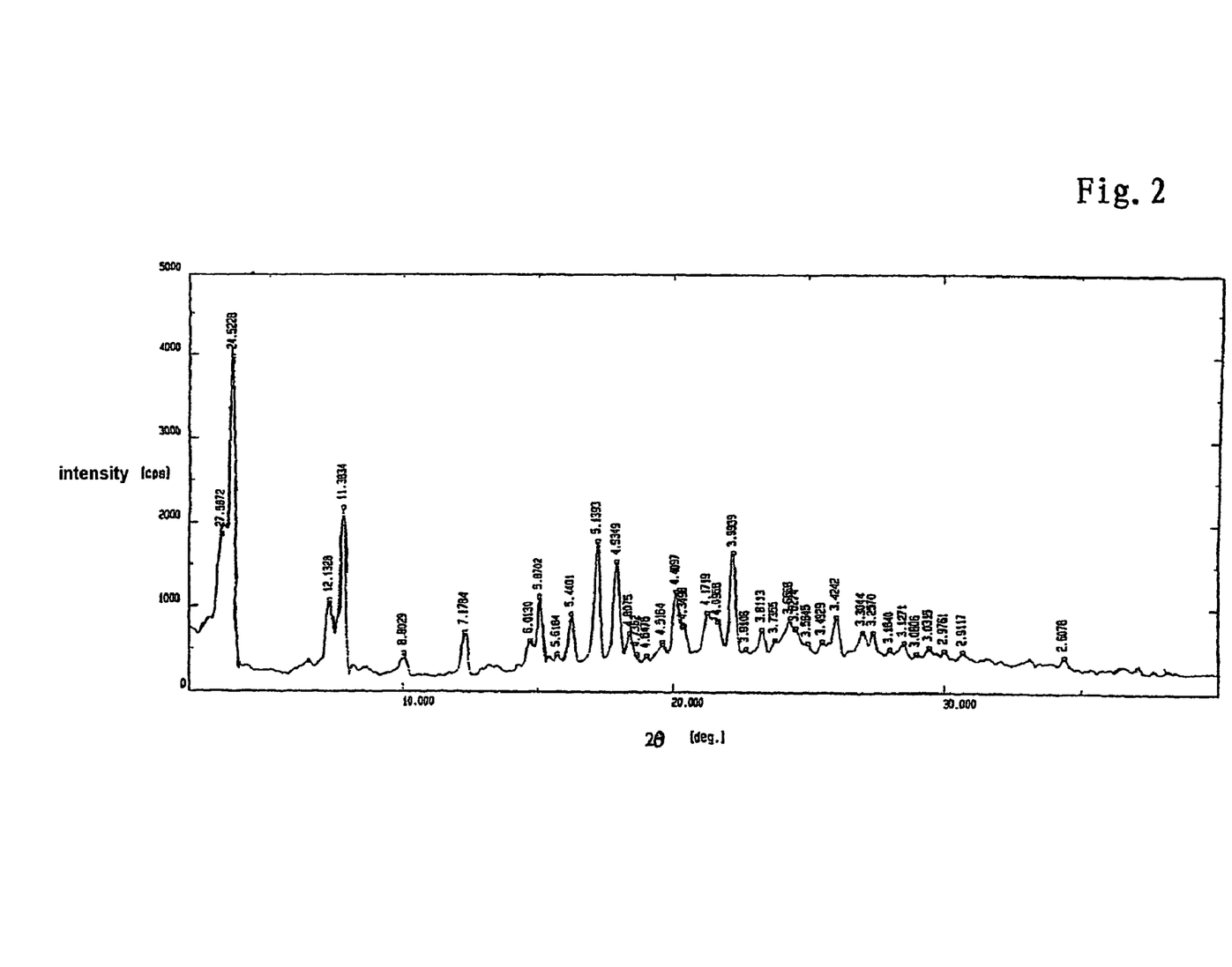
FIG. 2 shows X-ray diffraction pattern of the crystalline AD of the present invention.
Figure 3:
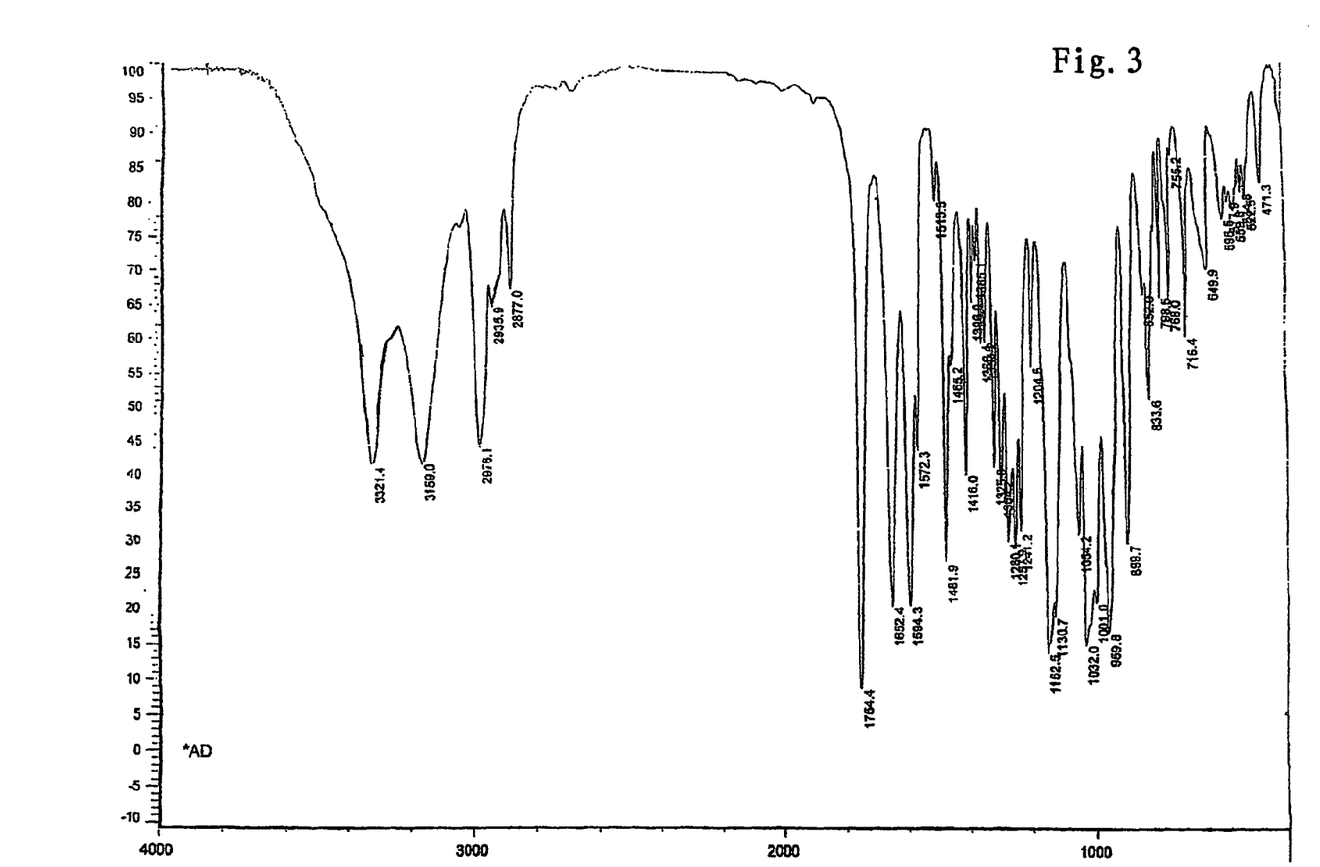
FIG. 3 shows Fourier Transform Spectrum of the crystalline AD of the present invention.
Figure 4:
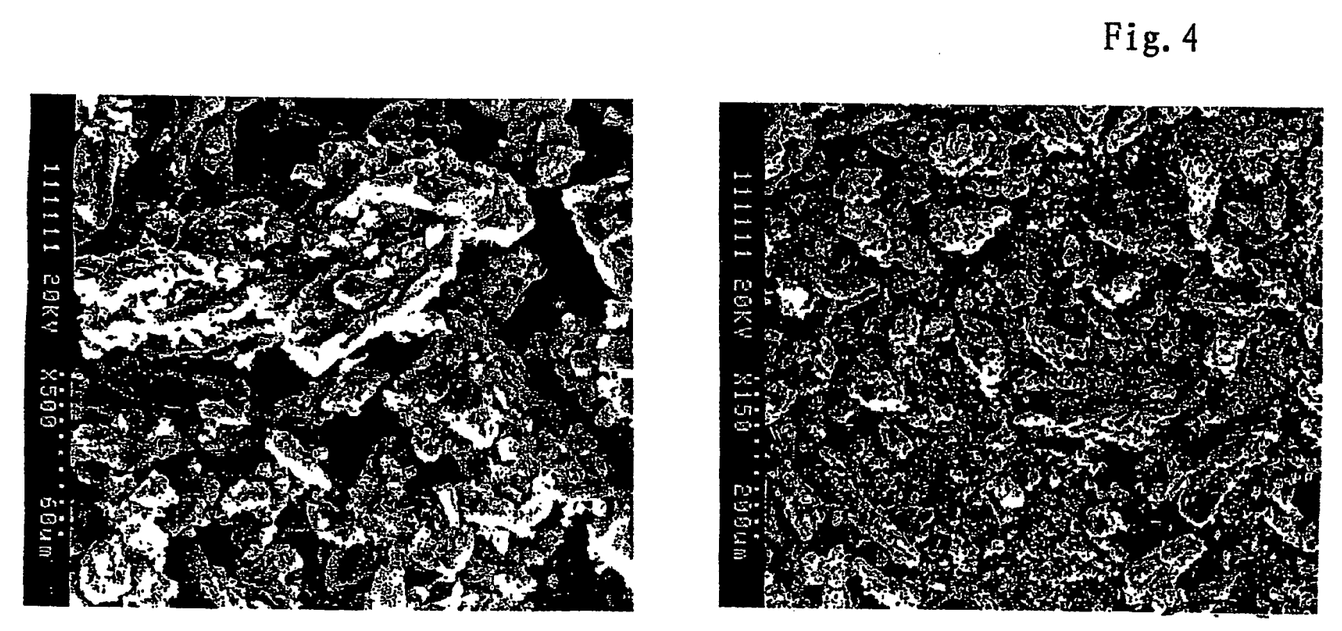
FIG. 4 show magnified picture of the crystalline AD of the present invention.

According to the present invention, the crystalline AD of this invention has a proper melting point. Further, by differential scanning calorimetry (DSC), infrared absorption spectrum (IR), powder X-Ray diffraction (XRD), melting point measurement, this crystalline AD is identified as an anhydrous crystal which is subtantially different from those already-existing ones in that: its endothermic peak in DSC thermogram is about 94.5° C. (see FIG. 1); its melting point is 94° C. –95° C.; its XRD pattern (see FIG. 2) usually shows a characteristic peak(s) expressed in terms of $2\theta$ at about 3.60, and/or about 7.28, and/or about 7.76, and/or about 12.32, and/or about 15.08, and/or about 16.28, and/or about 17.24, and/or about 17.96, and/or about 20.12, and/or about 21.40, and/or about 22.24, and more typical peak(s) at about 3.60, and/or about 7.28, and/or about 15.08, and/or about 17.24, and/or about 17.96, and/or about 20.12, and/or about 22.24; its Fourier. Transform Infrared Spectrum (FTIR) (see FIG. 3) shows a peak(s) at about $3320 \text{ cm}^{-1}$, about $3160 \text{ cm}^{-1}$, about $2975 \text{ cm}^{-1}$, about $2935 \text{ cm}^{-1}$, about $1755 \text{ cm}^{-1}$, about $1650 \text{ cm}^{-1}$, about $1595 \text{ cm}^{-1}$, about $1385 \text{ cm}^{-1}$, about $1355 \text{ cm}^{-1}$, and about $1152 \text{ cm}^{-1}$, and more typical peak(s) at about $3320 \text{ cm}^{-1}$, about $3160 \text{ cm}^{-1}$, about $2975 \text{ cm}^{-1}$, about $1755 \text{ cm}^{-1}$, and about $1650 \text{ cm}^{-1}$. The magnified photos of this crystalline AD are displayed in FIG. 4.

The raw material of AD in this invention can be prepared and recovered by the method described in Starrett et al., J. Med. Chem. (1994) 19: 1857-1864). Then the AD is eluted from the silica gel column with the mixture of methanol (about 4%) and methylene chloride (about 96%) and subjected to rotary evaporation under reduced pressure at about 35° C., and consequently the AD precipitates as a noncrystalline or an amorphous solid.

According to the present invention, the inventors have characterized the novel crystal or crystalline form of the present invention by well-accepted methods, including X-ray Diffraction (X-RD) and DSC. Usually a given crystalline form of a compound has a characteristic X-RD pattern.

Additional assays for identifying crystalline AD include differential scanning calorimetry (DSC), melting point measurement and infrared absorption spectroscopy (IR). DSC measures the thermal transition temperatures at which a crystal absorbs or releases heat due to the change of its crystal structure or melting. Successive analyses show that thermal transition temperatures and melting points are typically within a range of about 2° C., usually within about 1° C. In the present invention, when a compound is said to have a DSC peak or a melting point at a given value, it means that the DSC peak or the melting point is within 2° C.

DSC provides an alternative way for identifying different AD crystalline forms. Different crystalline forms may (at least partially) be identified by their different transition temperature profiles. IR measures absorption of infrared light caused by the particular chemical bonds associated with groups in the molecule that vibrate in response to light. DSC and IR can thus provide physicochemical information to describe AD crystals.

According to one embodiment, the crystalline AD of the present invention is prepared by a process comprising the following steps:
  a. Placing the AD produced by known methods in a round bottom flask;
  b. Adding organic solvent and dissolving the AD ultrasonically to form a AD solution;
  c. Spray drying the solution of step (b);
  d. Collecting the powder to obtain the crystalline AD.

In step (b), the organic solvent may be selected from the group consisting of anhydrous ethanol, methanol, acetone, acetoniril/di-n-butyl ether, and methylene chloride, wherein ethanol is preferred due to its low toxicity, low organic residue and good solubility for AD, which in turn results in less consumption of ethanol during the process. The concentration of organic solution is 100-300 g/L, preferably 200 g/L. In step (c), the inlet air temperature is set at 85-100° C., preferably 95° C. The measured inlet air temperature is 85-100° C., preferably 95° C. The measured outlet air temperature is 50-75° C., preferably 60° C. Pump output efficiency is 5-15%, preferably 8%. Air pump output efficiency is 70%-95%, preferably 85%. The airflow rate of the air compressor is 600 L/L-800 L/L, preferably 700 L/L.

Crystal is a solid substance having an ordered arrangement of all its constituent atom(s), molecule(s), or ion(s) in three dimensions. The crystals of the organic drug compounds basically belong to molecular lattice, but different processing conditions result in different crystals. Further, different crystals of the same drug compound can lead to marked differences in appearance, solubility, melting point, density, dissolution, and bio-availability etc., which accordingly will affect its stability and bioavailability. In view of this, studies on drug's crystalline forms have become an indispensable and important aspect in the development and authorization of a novel drug, the production and quality control of drug and the design before the final formulation of new drug.

According to this invention, the term "spray drying" means an instant drying method by atomizing the drug solution or extract into tiny liquid droplets in the high temperature air stream and drying the consequent droplets instantly. In terms of the power of nozzle, the devices can be divided into two types: the centrifugal spray drying tower and pressure spray drying tower.

According to this invention, the raw materials of AD can either be produced by prior art methods, or be commercially available.

The composition of the present invention comprises an therapeutically effective amount of the stable crystalline AD of the invention and pharmaceutically acceptable carriers or diluents. The composition of the present invention may be administered conveniently by any routes appropriate for administration, for example the composition may be administer orally, topically, parenterally, or inhalationally, preferably administered orally. Typically, the composition of the present invention can be obtained by using the crystalline AD and conventional carriers via any of the standardized methods well known in the art. Such methods include mixing, granulating, and tableting. It is well known by one skilled in the art that the selection of forms and natures of pharmaceutically acceptable carriers or excipients depends on many factors including the amount of the active ingredients to be mixed therewith, routes of administration, and other known factors. The composition comprises as active ingredient about 1-40% of AD by weight, preferably 5-30% by weight, wherein said AD comprises at least 70% of the crystalline AD of the present invention. It is understood that the composition of the present invention may optionally comprise a given amount of the amorphous AD.

The crystalline AD of the present invention is lipophilic. It will be absorbed readily after oral administration and in vivo hydrolyzed to its parent compound, 9-[(phosphonomethoxy)ethyl]adenine (PMEA, adefovir) rapidly. By far, the major dosage form containing AD are suspensions, tablets, and capsules. The studies have showed that in the aqueous suspensions containing AD, the bioavailability of PMEA is independent of the drug's solubility. Therefore, the suitable dosage forms of AD are tablets or capsules. The said drug may be pressed into solid unit dosage forms, such as pills, tablets or processed into capsules after being mixed with suitable pharmaceutically acceptable carriers. Conventional additives, such as fillers, colorants, and binders may be added in the preparation of unit dosage forms such as tablets. Typically, the dosage form for AIDS treatment comprises crystalline AD in an amount of 100-400 mg/unit, preferably 100-200 mg/unit. The dosage form for hepatitis B treatment comprises crystalline AD in an amount of 1-80 mg/unit, preferably 5-20 mg/unit.

According to this invention, said pharmaceutically acceptable carriers are either organic or inorganic carriers that can be administered together with active ingredients and may include the ones for solid pharmaceutical preparations, for example excipients, lubricants, binders, and disintegrants, and any pharmaceutically acceptable additives, for example colorants and sweetening agents.

The preferred excipients may be exemplified by lactose, sugar, D-mannitol, D-sorbitol, starch, α-starch, dextrine, crystalline cellulose, low-substituted hydroxypropylcellulose, sodium carboxymethylcellulose (CMC-Na), arabic gum, dextrine, amylopectin, light anhydrous silicic acid, synthesized aluminium silicate, aluminium-magnesium silicate etc.

The preferred lubricants may be exemplified by magnesium stearate, calcium stearate, talcum powders, silica gel etc.

The preferred binders may be exemplified by α-starch, sucrose, glutin, Arabic gum, methyl cellulose, carboxymethyl cellulose, sodium carboxymethyl cellulose, crystalline cellulose, sugar, D-mannitol, trehalose, dextrine, amylopectin, hydroxypropylcellulose, hydroxypropylmethylcellulose (HPMC), and pyrrolidone etc.

The preferred disintegrants may be exemplified by lactose, sugar, starch, carboxymethyl cellulose, calcium carboxymethyl cellulose, sodium carboxymethyl starch, light anhydrous silica acid, and low-substituted hydroxypropylcellulose.

The preferred colorants may be exemplified by water-soluble edible dyestuff citric acid yellow, for example edible red No. 2, edible yellow No. 4 and No. 5, edible blue No. 1 and No. 2; water-insoluble dyestuff, for example aluminium salt of the above-mentioned edible dyestuff citric acid yellow; naturally occurring dyestuffs such as beta-carotene, chlorophyll and iron red.

The preferred sweetening agents may be exemplified by saccharin sodium, potassium glycyrrhetinate dibasic, aspartame, and stevioside.

EXPERIMENT EXAMPLE

Kinetic Studies of the Plasma Concentration in Animals with Different Crystalline Forms of AD The experiment was carried out by orally administering to monkeys the drugs in order to investigate the in vivo absorption of two crystalline forms of AD: the novel crystalline AD of the present invention produced by Tianjin Kinsly pharmaceutical R & D Co. Ltd. and crystalline form I of AD prepared according to the method of GILEAD SCIENCES INC. The experiment provides useful clinical references for the application of novel crystalline AD.

1. Materials 1.1 Reagents

Methanol, CR level, Siyou Bio-medicine Technology Co. Ltd. (Tianjin, China), Batch number 020302101.

Deionized water, Semi-conductor Institute (Tianjin, China).

Phosphoric acid, AR level, The No. 2 Chemical Reagents Factory (Tianjin).

B7: The No. 2 Chemical Reagents Factory (Tianjin);

Trichloroacetic acid, Rugao Chemical Reagents Factory.

1.2 Apparatus

NL-200TPA analyzing scale, Shimadzu Inc. (Japan);

TGL-16B high-speed platform centrifuge, Shanghai Anting Scientific Device Factory (P. R. China);

The HPLC system equipped with WATERS 515 delivery system, WATERS 717 auto sampler, Spectra Ultraviolet detector, and ANASTAR chromatogram data workstation;

Xw-80A Vortex blender, Shanghai Jingke Industry Ltd.

1.3 Tested Agents

Tablets of novel crystalline form of AD, white, each of which contains 10 mg of adefovir, Tianjin Kinsly pharmaceutical R&D Co. Ltd., batch number 020320.

Tablets of AD crystalline form I, white, each of which contains 10 mg of adefovir, Tianjin Kinsly pharmaceutical R&D Co. Ltd., batch number 020225.

Adefovir (PMEA), as Chemical Reference Substance (CRS), Tianjin Kinsly pharmaceutical R&D Co. Ltd.

1.4 Animals

Macaques, weighing from 5 kg to 8 kg (certificate No: 2001-03, approved by Beijing Forestry Administration in the document of [2001] 83) were provided by Xie'er Animal Health Caring Science and Technology Co. Ltd (Beijing, P. R. China).

2. Testing Methods

As the pro-drug of adefovir, AD is the bis-pivaloyloxymethyl ester of adefovir, which increases the in vivo bioavailability of orally administered adefovir. AD can be rapidly metabolized into PMEA, rendering it undetectable in blood. Thus the concentration of its parent compound was measured.

a. HPLC Conditions were as Follows:

Mobile phase: 0.2% phosphoric acid-methanol-$B_7$ (97:3:0.5) degassed and filtrated through 0.45 μm milipore filter.

Flow rate: 1.0 ml/min.

Stationary phase: $C_{18}$-column (4.6×250 mm) packed with 5μ fillers, Tianjin Tianhe Chromatogram Inc, the column temperature from 18° C. to 22° C.

Detection: the UV detection wavelength $\lambda=260$ nm (0.01AUFS)

Injection volume: 30 μL.

b. Analysis of Blood

A given volume of serum was taken and an equal volume of 10% trichloroacetic acid was added. The mixture was shaken thoroughly and kept still for more than 30 min to precipitate the proteins, then centrifuged at 10000 rpm for 2 min. The precipitates were separated and 30 μL of the supernat was removed for injection.

Standard curve: 25 μL of PMEA RSD solution of different concentration was added into 0.475 ml blank monkey serum respectively to obtain a series of standard serum samples with the final concentration of 0, 20, 50, 100, 200, 500, 1000, and 2000 ng/m in duplicate. An equal volume of 10% trichloroacetic acid was added into samples to precipitate the protein as mentioned above. 30 μL of the supernate was remove for injection.

Recovery rate: 25 μL of PMEA RSD solution of different concentration was added into 0.475 ml blank monkey serum to obtain a series of standard serum samples with the concentration of 100, 500, and 2000 ng/m in quintuplicate. The protein was precipitated as mentioned above and 30 μL of the supernate was removed for injection. Absolute recovery rate was calculated with reference to the sample of control.

Within-day and day-to-day variation: standard serum samples of 100, 500, and 2000 ng/m were prepared and treated as in the measurement of recovery rate, measured for six times within a day to obtain within-day variation, and measured duplicate samples on four successive days to obtain day-to-day variation.

3. Determination of Plasma Concentration of the Drug

The experiment was started one week after intestinal worms were dispelled from the animals. Eight animals were randomly assigned into two groups, each consisting of four animals. The animals were fasted for 12 h and were orally administered the novel crystalline form of AD for one group or crystalline form I of AD for another group at a dose of 20 mg/kg together with 200 ml of water. 2 hours after administration, the animals were fed in a fixed quantity. 2.0 ml samples of whole blood were collected from the elbow veins before administration and 10, 20, 30, 45 min and 1, 2, 4, 6, 8, 12, and 24 h after administration. The serum was separated and freeze-stored for measurement. A cross-experiment was done similarly 2 weeks later.

4. Results and Data Processing

The pharmacokinetic parameters were calculated based on the plasma concentrations at different time points. The time to peak concentration (Tpeak) and the maximum concentration (Cmax) used the measured value. The terminal phase elimination rate constant (Ke) was obtained by fitting the linear section of the curve of logarithm of the plasma concentration of drug in terminal phase versus time and the terminal phase clearance half life time ($T_{1/2}$) was calculated by dividing 0.693 by Ke. $AUC_{0-t}$ was calculated according to the trapezoid rule.

Apparent volume of distribution (Vd)=dosage/(AUCXKe);

Total Clearance (CL)=dosage/AUC.

Comparison of the data of the two crystalline form: Data of Cmax, Ke, $T_{1/2}$ and $AUC_{0-t}$ were statistically processed by t test, while Tpeak was processed by non-parametric test. In addition, Comparison of bio-equivalence was carried out based on $C_{max}$ and $AUC_{0-t}$ by using two one-sided t test.

4.1 Results of Methodology a. Standard Curve

The retention time of adefovir was about 12 min. The regression analysis of the peak area versus concentration (0 to 2000 ng/ml) of standard serum samples was carried out and the results were shown in Table 1.

TABLE 1

The standard curve of adefovir in serum

|  | 20 | 50 | 100 | 200 | 500 | 1000 | 2000 |
|---|---|---|---|---|---|---|---|
| 1 | 660 | 1291 | 2643 | 5333 | 11148 | 23729 | 47287 |
| 2 | 671 | 1385 | 2499 | 5056 | 11271 | 21994 | 48006 |
| Average | 665.5 | 1338 | 2571 | 5194.5 | 11209.5 | 22861.5 | 47646.5 |

C = 0.04242 A-2.0315 (r = 0.9996); C: concentration (ng/ml); A: Peak Area; detection limit: 20 ng/ml.

b. Recovery Rate

Trichloroacetic acid was added into standard serum samples with the concentration of 100, 500 and 2000 ng/ml in quintuplicate to precipitate the protein and the peak areas of the treated sample versus those of untreated samples gave the absolute recovery rate of 91.9%, 93.9%, and 96.7%. The average was 94.2±2.4%.

c. Within-Day and Day-To-Day Variation

Studies showed that adefovir had a good performance in accuracy and repeatability within a day. Moreover, the treated supernate was so stable that there were hardly any variations in the concentration of adefovir within three days. All the variation coefficients were less than 10%.

4.2 Determination of Plasma Concentrations of the Drug and Fitting of Pharmacokinetic Parameters Eight macaques were assigned into two groups, group for the novel crystalline form and the group for crystalline form I. The animals were administered according to an open randomized crossover scheme. Afterward, adefovir concentrations in serum were measured at the predetermined time points. The results showed that the plasma concentrations of two crystalline forms at every time points were very close (see Table2). Pharmacokinetic parameters were calculated based on the curve of the plasma concentration versus time after oral administration of adefovir (see Table3).

TABLE 2-1

Adefovir concentrations in serum at different time points after oral administration of novel crystalline form Plasma concentrations versus time (ng/ml)

| No. | 0.167 h | 0.333 h | 0.5 h | 0.75 h | 1 h | 2 h | 4 h | 6 h | 8 h | 12 h | 24 h |
|---|---|---|---|---|---|---|---|---|---|---|---|
| 1 | 53.2 | 154.1 | 448.9 | 195.6 | 132.7 | 117.7 | 85.0 | 85.9 | 79.0 | 59.4 | 41.6 |
| 2 | 60.0 | 176.3 | 529.4 | 393.7 | 134.1 | 105.3 | 77.2 | 57.3 | 55.6 | 80.5 | 59.4 |
| 3 | 76.9 | 270.7 | 389.5 | 55.0 | 273.4 | 260.3 | 191.0 | 145.3 | 119.2 | 72.2 | 19.2 |
| 4 | 51.8 | 186.7 | 952.4 | 507.6 | 260.3 | 221.6 | 205.1 | 177.0 | 158.9 | 112.6 | 99.3 |
| 5 | 105.0 | 258.5 | 403.1 | 306.8 | 231.8 | 196.1 | 140.9 | 114.5 | 96.9 | 82.1 | 76.3 |
| 6 | 103.9 | 248.8 | 398.3 | 538.7 | 374.7 | 255.0 | 184.8 | 95.2 | 112.0 | 46.1 | 28.3 |
| 7 | 78.3 | 190.1 | 541.8 | 360.6 | 269.4 | 241.4 | 198.9 | 141.2 | 89.4 | 64.5 | 53.1 |
| 8 | 64.9 | 125.9 | 396.0 | 278.8 | 233.5 | 196.1 | 175.8 | 141.3 | 110.7 | 44.8 | 36.6 |
| ASD | 74.3 | 201.4 | 507.4 | 392.0 | 238.8 | 199.3 | 157.3 | 119.7 | 102.7 | 70.3 | 51.7 |
|  | 19.6 | 49.0 | 177.5 | 123.1 | 73.6 | 55.5 | 47.6 | 36.3 | 28.7 | 20.7 | 24.7 |

ASD, Average Standard Deviation

TABLE 2-2

Adefovir concentrations in serum at different time points after oral administration of crystalline form I Plasma concentrations versus time (ng/ml)

| No. | 0.167 h | 0.333 h | 0.5 h | 0.75 h | 1 h | 2 h | 4 h | 6 h | 8 h | 12 h | 24 h |
|---|---|---|---|---|---|---|---|---|---|---|---|
| 1 | 100.6 | 299.7 | 915.4 | 383.9 | 328.2 | 280.1 | 248.5 | 207.3 | 144.3 | 86.9 | 61.6 |
| 2 | 84.8 | 194.0 | 432.2 | 319.0 | 294.4 | 264.7 | 233.8 | 171.6 | 163.7 | 12.97 | 53.8 |
| 3 | 67.2 | 196.7 | 376.4 | 412.3 | 306.9 | 278.2 | 129.9 | 139.3 | 118.4 | 57.8 | 22.1 |
| 4 | 66.6 | 148.0 | 397.9 | 305.2 | 196.6 | 161.3 | 89.3 | 102.0 | 82.9 | 70.1 | 36.8 |
| 5 | 90.1 | 225.0 | 402.2 | 257.2 | 226.4 | 132.9 | 134.1 | 105.2 | 93.8 | 72.6 | 56.6 |
| 6 | 79.8 | 239.8 | 758.4 | 372.3 | 322.7 | 204.2 | 168.7 | 136.5 | 120.4 | 76.2 | 38.6 |
| 7 | 64.1 | 208.2 | 366.2 | 255.0 | 202.8 | 201.8 | 154.8 | 81.6 | 77.4 | 70.8 | 51.1 |
| 8 | 62.6 | 371.8 | 698.1 | 502.1 | 403.2 | 320.5 | 261.0 | 231.1 | 132.9 | 124.1 | 33.5 |

TABLE 2-2-continued

Adefovir concentrations in serum at different time points after oral administration of crystalline form I

| | Plasma concentrations versus time (ng/ml) | | | | | | | | | | |
|---|---|---|---|---|---|---|---|---|---|---|---|
| No. | 0.167 h | 0.333 h | 0.5 h | 0.75 h | 1 h | 2 h | 4 h | 6 h | 8 h | 12 h | 24 h |
| ASD | 77.0 | 235.4 | 546.7 | 350.9 | 285.2 | 230.5 | 177.5 | 146.8 | 116.7 | 86.0 | 44.3 |
| | 14.0 | 70.1 | 218.3 | 83.9 | 71.6 | 65.3 | 62.9 | 52.8 | 30.4 | 26.5 | 13.5 |

ASD, Average Standard Deviation

TABLE 3

Pharmacokinetic parameters calculated based on the curve of adefovir plasma concentrations versus time after administration of AD

| Group | No. | Tpeak h | Cmax ng/ml | Ke l/h | T1/2 h | Vd L | $AUC_{0-t}$ ng·h/ml | CL Ml/h |
|---|---|---|---|---|---|---|---|---|
| Novel crystalline form | 1 | 0.50 | 448.9 | 0.043 | 16.0 | 265.9 | 1735.9 | 11521.7 |
| | 2 | 0.50 | 529.4 | 0.046 | 14.9 | 224.6 | 1921.2 | 10410.0 |
| | 3 | 0.75 | 555.0 | 0.117 | 5.9 | 67.1 | 2556.8 | 7822.3 |
| | 4 | 0.50 | 403.1 | 0.037 | 18.4 | 147.5 | 3593.4 | 5565.7 |
| | 5 | 0.50 | 403.1 | 0.037 | 18.8 | 211.8 | 2567.8 | 7788.8 |
| | 6 | 0.75 | 538.7 | 0.097 | 7.2 | 89.1 | 2318.3 | 8627.0 |
| | 7 | 0.50 | 541.8 | 0.068 | 10.2 | 115.1 | 2554.7 | 7828.6 |
| | 8 | 0.50 | 396.3 | 0.082 | 8.4 | 112.4 | 2162.8 | 9247.2 |
| | ASD | 0.56 | 545.7 | 0.066 | 12.5 | 154.2 | 2426.4 | 8601.4 |
| | | 0.12 | 176.4 | 0.030 | 5.2 | 71.6 | 564.3 | 1824.3 |
| Crystalline form I | 1 | 0.5 | 402.2 | 0.072 | 9.6 | 125.6 | 2214.1 | 9033.0 |
| | 2 | 0.5 | 785.4 | 0.071 | 9.8 | 107.3 | 2624.4 | 7620.7 |
| | 3 | 0.75 | 366.2 | 0.107 | 6.5 | 85.8 | 2188.0 | 9140.8 |
| | 4 | 0.5 | 698.1 | 0.058 | 12.0 | 95.0 | 3647.5 | 5483.3 |
| | 5 | 0.5 | 915.4 | 0.041 | 17.0 | 145.1 | 3379.4 | 5918.1 |
| | 6 | 0.5 | 432.2 | 0.076 | 9.2 | 76.6 | 3452.3 | 5793.2 |
| | 7 | 0.5 | 412.3 | 0.054 | 12.8 | 158.8 | 2317.8 | 8628.9 |
| | 8 | 0.5 | 397.9 | 0.102 | 6.8 | 99.9 | 1967.0 | 10167.8 |
| | ASD | 0.53 | 551.21 | 0.072 | 10.5 | 117.0 | 2723.8 | 7723.2 |
| | | 0.09 | 214.62 | 0.023 | 3.4 | 45.6 | 666.3 | 1794.1 |

ASD: Average Standard Deviation
Note:
there was no statistical significance between groups on the basis of comparison of the corresponding parameters of the groups.

After oral administration of two different crystalline forms of AD at a dose of 20 mg/kg to animals, pharmacokinetic parameters were calculated based on the curve of plasma concentration of adefovir versus time. The average $T_{peak}$ of two crystalline forms were 0.56 h and 0.53 h respectively, the average peak concentration 545.69 ng/ml and 551.21 ng/ml respectively, the average elimination half-life time 12.5 h and 10.5 h respectively, the average $AUC_{O-T}$ 2426.37 ng·h/ml and 2723.82 ng·h/ml respectively, the average apparent volume of distribution (Vc) 19.74 L and 17.50 L respectively, and the average total clearance rate 8601.41 L/h and 7723.21 L/h respectively. So the results showed that there was no statistical significance between the differences of pharmacokinetic parameters of two groups.

4.3 Statistical Analysis

The difference in absorption between two crystalline forms was demonstrated in Table 4 by comparing the value of the Cmax and $AUC_{0-t}$.

TABLE 4-1

Bioavailability of adefovir of the novel crystalline form versus Crystalline form I

| $AUC_{0-t}$ (ng·h/ml) | | Bioavailability | Cmax (ng/ml) | |
|---|---|---|---|---|
| Novel form | Form I | (%) | Novel form | Form I |
| 1735.9 | 2214.1 | 0.78 | 448.8 | 402.2 |
| 1921.2 | 2624.4 | 0.73 | 529.4 | 785.4 |
| 2556.8 | 2188.0 | 1.17 | 555.0 | 366.2 |
| 3593.4 | 3647.5 | 0.99 | 952.4 | 689.1 |
| 2567.8 | 3379.4 | 0.76 | 403.1 | 915.4 |
| 2318.3 | 3452.3 | 0.67 | 538.7 | 432.2 |
| 2554.7 | 2317.8 | 1.10 | 541.8 | 412.3 |
| 2162.8 | 1967.0 | 1.10 | 396.2 | 397.9 |
| 2426 | 2724 | 0.91 | 545.7 | 551.21 |
| 564 | 666 | 0.20 | 176.4 | 214.62 |

TABLE 4-1-continued

|  | Sum of square | Degree of freedom | Average variance | F | P |
|---|---|---|---|---|---|
| Result of variance analysis of adefovir bioavailability between two crystalline ADs | | | | | |
| Total variance | 5690686.9 | 15 | | | |
| Duration | 26099.3 | 1 | 26099.29 | 0.15 | 0.72 |
| Preparations | 353906.7 | 1 | 353906.67 | 1.98 | 0.21 |
| Individuals | 4239970.1 | 7 | 605710.01 | 3.39 | 0.08 |
| Total error | 1070710.9 | 6 | 178451.82 | | |
| Result of variance analysis of adefovir peak concentrations between two different crystalline ADs | | | | | |
| Total variance | 540406.6 | 15 | | | |
| Duration | 16362.5 | 1 | 16362.50 | 0.28 | 0.61 |
| Preparations | 122.1 | 1 | 122.15 | 0.002 | 0.96 |
| Individuals | 179219.1 | 7 | 25602.73 | 0.45 | 0.84 |
| Total error | 344702.9 | 6 | 57150.48 | | |

CONCLUSION

After oral administration of the tablets containing two different crystalline ADs at a dose of 20 mg/kg to monkeys, the plasma level of the adefovir was measured. As shown by the results, the parameters including average $T_{peak}$, peak concentration ($C_{peak}$), $T_{1/2}$ and $AUC_{0-t}$ between two different crystalline ADs groups were basically identical. Statistic analysis indicated that differences of both $C_{peak}$ and $AUC_{0-t}$ between two forms were not statistically significant.

EXAMPLES

The following examples further elaborate the present invention and do not by any means limit the invention.

Example 1

Preparation of Crystalline AD

The raw AD was prepared according to the representative method as described (Starrett et al., J. Med. Chem. (1994) 37:1857-1864) and the novel crystalline AD was prepared by spray drying method as follows:
  a. Placing about 20 g AD produced by aforementioned method in a 150 ml round bottom flask;
  b. Adding 100 ml anhydrous ethanol and dissolving AD ultrasonically to form a solution of AD of 200 g/L;
  c. Spray drying the AD solution in ethanol of step (b);
  d. Collecting the powder, which was identified (HPLC) as AD of 99.2% purity.

The conditions of the spray drying: The inlet air temperature was set at 95° C. The measured inlet air temperature was 95° C. The measured outlet air temperature was 60° C. Pump output efficiency was 8%. Air pump output efficiency was 85%. The airflow rate of the air compressor was at 700 L/L.

Validation by Spectrum:

In terms of the crystalline AD prepared by foregoing method, an endothermic peak at about 94.5° C. was detected in DSC thermogram; characteristic peaks expressed in terms of 2θ at about 3.60, about 7.28, about 7.76, about 12.32, about 15.08, about 16.28, about 17.24, about 17.96, about 20.12, about 21.40, and about 22.24 were shown in powder XRD pattern; peaks at about 3320 $cm^{-1}$, about 3160 $cm^{-1}$, about 2975 $cm^{-1}$, about 2935 $cm^{-1}$, about 1755 $cm^{-1}$, about 1650 $cm^{-1}$, about 1595 $cm^{-1}$, about 1385 $cm^{-1}$, about 1355 $cm^{-1}$, and about 1152 $cm^{-1}$ were shown in Fourier Transform Infrared Spectrum (FTIR).

Example 2

Preparation of Crystalline AD

The raw AD was prepared according to the representative method as described (Starrett et al., J. Med. Chem. (1994) 37:1857-1864) and the novel crystalline AD was prepared by spray drying method as follows:
  a. Placing about 10 g of AD produced by aforementioned method in a 150 ml round bottom flask;
  b. Adding 100 ml acetoniril/di-n-butyl ether and dissolving AD ultrasonically to form a solution of AD of 100 g/L;
  c. Spray drying the organic solution of step (b);
  d. Collecting the powder, which was identified (HPLC) as AD of 99.0% purity.

The conditions of the spray drying: The inlet air temperature was set at 85° C. The measured inlet air temperature was 85° C. The measured outlet air temperature was 50° C. Pump output efficiency was 5%. Air pump output efficiency was 70%. The airflow rate of the air compressor was at 600 L/L.

Validation by Spectrum:

In terms of the crystalline AD prepared by foregoing method, an endothermic peak at about 94.5° C. was detected in DSC thermogram; peaks expressed in terms of 2θ at about 3.60, about 7.28, about 7.76, about 12.32, about 15.08, about 16.28, about 17.24, about 17.96, about 20.12, about 21.40, and about 22.24 were shown in powder XRD pattern; peaks at about 3320 $cm^{-1}$, about 3160 $cm^{-1}$, about 2975 $cm^{-1}$, about 2935 $cm^{-1}$, about 1755 $cm^{-1}$, about 1650 $cm^{-1}$, about 1595 $cm^{-1}$, about 1385 $cm^{-1}$, about 1355 $cm^{-1}$ and about 1152 $cm^{-1}$ were shown in Fourier Transform Infrared Spectrum (FTIR).

Example 3

Preparation of Crystalline AD

The raw AD was prepared according to the representative method as described (Starrett et al., J. Med. Chem. (1994) 37:1857-1864) and the novel crystalline AD was prepared by spray drying method as follows:
  a. Placing about 30 g of AD produced by aforementioned method in a 150 ml round bottom flask;
  b. Adding 100 ml methylene chloride and dissolving AD ultrasonically to form a solution of AD of 300 g/L;
  c. Spray drying the organic solution of step (b);
  d. Collecting the powder, which was identified (HPLC) as AD of 95.0% purity.

The conditions of the spray drying: The inlet air temperature was set at 100° C. The measured inlet air temperature was 100° C. The measured outlet air temperature was 75° C. Pump output efficiency was 15%. Air pump output efficiency was 80%. The airflow rate of the air compressor was at 800 L/L.

Validation by Spectrum:

In terms of the crystalline AD prepared by foregoing method, an endothermic peak at about 94.5° C. was detected in DSC thermogram; peaks expressed in terms of $2^\theta$ at about 3.60, about 7.28, about 7.76, about 12.32, about 15.08, about 16.28, about 17.24, about 17.96, about 20.12, about 21.40, and about 22.24 were shown in powder XRD pattern; peaks at about 3320 $cm^{-1}$, about 3160 $cm^{-1}$, about 2975 $cm^{-1}$, about 2935 $cm^{-1}$, about 1755 $cm^{-1}$, about 1650 $cm^{-1}$, about 1595 cm⁻¹, about 1385 cm⁻¹, about 1355 cm⁻¹ and about 1152 cm⁻¹ were shown in Fourier Transform Infrared Spectrum (FTIR).

Example 4

Preparation of Crystalline AD

The raw AD was prepared according to the representative method as described (Starrett et al., J. Med. Chem. (1994) 37:1857-1864) and the novel crystalline AD was prepared by spray drying method as follows:
  a. Placing about 25 g of AD produced by aforementioned method in a 150 ml round bottom flask;
  b. Adding 100 ml acetone and dissolving AD ultrasonically to form a solution of AD of 250 g/L;
  c. Spray drying the organic solution of step (b);
  d. Collecting the powder, which was identified (HPLC) as AD of 98.0% purity.

The conditions of the spray drying: The inlet air temperature was set at 90° C. The measured inlet air temperature was 87° C. The measured outlet air temperature was 65° C. Pump output efficiency was 12%. Air pump output efficiency is 78%. The airflow rate of the air compressor was at 700 L/L.

Validation by Spectrum:

In terms of the crystalline AD prepared by foregoing method, an endothermic peak at about 94.5° C. was detected in DSC thermogram; peaks expressed in terms of 2θ at about 3.60, about 7.28, about 7.76, about 12.32, about 15.08, about 16.28, about 17.24, about 17.96, about 20.12, about 21.40, and about 22.24 were shown in powder XRD pattern; peaks at about 3320 cm⁻¹, about 3160 cm⁻¹, about 2975 cm⁻¹, about 2935 cm⁻¹, about 1755 cm⁻¹, about 1650 cm⁻¹, about 1595 cm⁻¹, about 1385 cm⁻¹, about 1355 cm⁻¹, and about 1152 cm⁻¹ were shown in Fourier Transform Infrared Spectrum (FTIR).

Example 5

Preparation of Crystalline AD

The raw AD was prepared according to the representative method as described (Starrett et al., J. Med. Chem. (1994%) 37: 1857-1864) and the novel crystalline AD was prepared by spray drying method as follows:
  a. Placing about 18 g of AD produced by aforementioned method in a 150 ml round bottom flask;
  b. Adding 100 ml methanol and dissolving AD ultrasonically to form a solution of AD of 180 g/L;
  c. Spray drying the organic solution of step (b);
  d. Collecting the powder, which was identified (HPLC) as AD of 99.0% purity.

The conditions of the spray drying: The inlet air temperature was set at 88° C. The measured inlet air temperature was 85° C. The measured outlet air temperature was 68° C. Pump output efficiency was 9%. Air pump output efficiency was 90%. The airflow rate of the air compressor was at 680 L/L.

Validation by Spectrum:

In terms of the crystalline AD prepared by above method, an endothermic peak at about 94.5° C. was detected in DSC thermogram; peaks expressed in terms of 2θ at about 3.60, about 7.28, about 7.76, about 12.32, about 15.08, about 16.28, about 17.24, about 17.96, about 20.12, about 21.40 and about 22.24 were shown in powder XRD pattern; peaks at about 3320 cm⁻¹, about 3160 cm⁻¹, about 2975 cm⁻¹, about 2935 cm⁻¹, about 1755 cm⁻¹, about 1650 cm⁻¹, about 1595 cm⁻¹, about 1385 cm⁻¹, about 1355 cm⁻¹ and about 1152 cm⁻¹ were shown in Fourier Transform Infrared Spectrum (FTIR).

Example 6

Tablets Containing the Vrystalline AD

The tablets containing the crystalline AD of example 1 were prepared according to the formula as describes below, and each of the tablets contains 10 mg AD.

| Component | amount |
| --- | --- |
| Crystalline AD | 10 mg |
| Lactose | 65 mg |
| Pregelatinized starch | 25 mg |
| Croscarmellose Sodium | 3 mg |
| Colloidal silicon dioxide | 0.25 mg |
| Magnesium Stearate | 0.30 mg |

The crystalline AD, lactose, pregelatinized starch and croscarmellose sodium were respectively passed through 65-mesh screen for later use. The AD was weighed according to the amount as described in the formula and mixed with other adjuvants in a manner of increasing the amounts proportionally. The mixture was passed through 65-mesh screen for three times. The angle of repose was measured as less than 30°. After content tested and weight determined, tablets were prepared by direct compression of the mixture using a 6.5 mm-diameter flat punch pin.

Example 7

Capsules Containing the Crystalline AD

The capsules containing the crystalline AD of example 1 were prepared according to the formula as describes below, and each of the capsules contains 10 mg AD.

| Component | amount |
| --- | --- |
| Crystalline AD | 10 mg |
| Lactose | 135 mg |
| Pregelatinized starch | 25 mg |
| Croscarmellose Sodium | 3 mg |
| Colloidal silicon dioxide | 0.25 mg |
| Magnesium Stearate | 0.30 mg |

The crystalline AD, lactose, pregelatinized starch, croscarmellose sodium were respectively passed through 65-mesh screen for later use. The AD was weighed according to the amount as described in the formula and mixed with other adjuvants in a manner of increasing the amounts proportionally. The mixture was passed through 65-mesh screen for three times. The angle of repose was measured as less than 300. After content tested and capacity determined, capsules were prepared by loading the mixture into No. 3 capsules.

What is claimed is:

1. A crystalline adefovir dipivoxil, characterized in that it has characteristic peaks expressed in terms of 2θ at about 3.60, about 7.28, about 15.08, about 17.24, about 17.96, about 20.12, and about 22.24 in X-ray powder diffraction pattern with Cu target radiation, an endothermic peak at about 94.5° C. in DSC thermogram, a melting point at 94° C. to 95° C., and peaks at about 3320 cm$^{-1}$, about 3160 cm$^{-1}$, about 2975 cm$^{-1}$, about 1755 cm$^{-1}$, and about 1650 cm$^{-1}$ in Fourier Transform Infrared Spectrum.

2. A composition comprising the crystalline adefovir dipivoxil of claim 1 and one or more pharmaceutically acceptable carriers or excipients.

3. The composition of claim 2 in unit dosage form wherein each dosage unit contains 100-400 mg crystalline adefovir dipivoxil.

4. The composition of claim 2 in unit dosage form wherein each dosage unit contains 1-80 mg crystalline adefovir dipivoxil.

5. A process for preparing the crysyalline adefovir dipivoxil of claim 1, comprising:
  a. Placing adefovir dipivoxildipivoxil in a round bottom flask;
  b. Adding organic solvent and dissolving adefovir dipivoxil ultrasonically to form an adefovir dipivoxil solution;
  c. Spray drying the adefovir dipivoxil solution formed by step b to form a powder; and
  d. Collecting the powder to obtain the crystalline adefovir dipivoxil.

6. The process of claim 5, wherein said organic solvent of step (b) is selected from the group consisting of anhydrous ethanol, methanol, acetone, acetonitrile/di-n-butyl ether, and methylene chloride and the formed adefovir dipivoxil solution has an adefovir dipivoxil concentration of 100-300 g/L; in step (c),the inlet air temperature is set at 85-100° C., the measured inlet air temperature is 85-100° C.; the measured outlet air temperature is 50-75° C.; pump output efficiency is 5-15step (c),the inlet air temperature is set at 85-100° C., the emasured inlet air temperature is 5-15%; air pump output efficiency is 70%-95%; and the rate of airflow of the air compressor is at 600 L/L-800 L/L.

7. The process of claim 5, wherein said organic solvent of step (b) is ethanol and said adefovir dipivoxil solution has an adefovir dipivoxil concentration of 200 g/L; in step (c), said inlet air temperature is set at 95° C., the measured inlet air temperature is 95° C.; the measured outlet air temperature is 60° C. ;pump output efficiency is 8%; air pump output efficiency is 85%; and the rate of airflow of the air compressor is at 700 L/L.

* * * * *